(12) United States Patent
Mochizuki et al.

(10) Patent No.: US 9,163,149 B2
(45) Date of Patent: Oct. 20, 2015

(54) IMPLANT MATERIAL

(75) Inventors: Akira Mochizuki, Numazu (JP); Yuki Nitta, Hiroshima (JP); Keishi Okamoto, Hiroshima (JP); Tatsuyuki Nakatani, Hiroshima (JP)

(73) Assignee: TOYO ADVANCED TECHNOLOGIES CO., LTD., Hiroshima (JP)

( * ) Notice: Subject to any disclaimer, the term of this patent is extended or adjusted under 35 U.S.C. 154(b) by 479 days.

(21) Appl. No.: 13/807,267

(22) PCT Filed: Jun. 30, 2011

(86) PCT No.: PCT/JP2011/003756
§ 371 (c)(1),
(2), (4) Date: Dec. 27, 2012

(87) PCT Pub. No.: WO2012/001983
PCT Pub. Date: Jan. 5, 2012

(65) Prior Publication Data
US 2013/0108879 A1    May 2, 2013

(30) Foreign Application Priority Data

Jun. 30, 2010    (JP) .................. 2010-150093

(51) Int. Cl.
*A61F 2/28* (2006.01)
*A61F 2/30* (2006.01)
*A61L 27/30* (2006.01)
(Continued)

(52) U.S. Cl.
CPC ... *C09D 5/00* (2013.01); *A61C 5/08* (2013.01); *A61C 8/0012* (2013.01); *A61C 8/0013* (2013.01); *A61C 13/01* (2013.01); *A61C 13/08* (2013.01); *A61K 6/0044* (2013.01); *A61L 27/303* (2013.01); *A61F 2/30767* (2013.01); *A61F 2002/3093* (2013.01); *A61L 2430/02* (2013.01); *A61L 2430/12* (2013.01); *Y10T 428/31678* (2015.04)

(58) Field of Classification Search
None
See application file for complete search history.

(56) References Cited

U.S. PATENT DOCUMENTS

2010/0247917 A1    9/2010    Nitta et al.

FOREIGN PATENT DOCUMENTS

JP    2002-143185 A    5/2002
JP    2002-204825 A    7/2002
(Continued)

OTHER PUBLICATIONS

Nitta et al., Diamond-like carbon thin film with controlled zeta potential for medical material application, Diamond & Related Materials 17(2008) pp. 1972-1976.
Zhan et al., Study of biocompatibility for Ti implants with DLC coating, Chinese Journal of Materials Research, vol. 13, No. 4, pp. 405-408, (Aug. 1999).
Li et al., "The Study on Biocompatibility of Diamond-like Carbon Coated Nickel—tinanium shape memory alloy with osteoblasts cultured in vitor," Chinese Journal of Reparative and Reconstructive Surgery, 2006, vol. 20, No. 1, pp. 5-8.
(Continued)

*Primary Examiner* — Ramsey Zacharia
(74) *Attorney, Agent, or Firm* — Knobbe Martens Olson & Bear LLP

(57) ABSTRACT

An implant material includes: a base material 10; and a carbonaceous film 20 provided on a surface of the base material 10. The carbonaceous film 20 includes carbon atoms, oxygen atoms, and nitrogen atoms in a surface thereof, and the carbon atoms are bonded to the oxygen atoms to form carboxyl carbon and carbon having a single bond with oxygen. In the surface of the carbonaceous film 20, a content of nitrogen atoms is greater than or equal to 8.0 at. %, a content of carbon having a single bond with oxygen is greater than or equal to 5.4%, and a content of carboxyl carbon is less than or equal to 3.1%.

8 Claims, 5 Drawing Sheets

(51) Int. Cl.
  *C09D 5/00*    (2006.01)
  *A61C 8/00*    (2006.01)
  *A61K 6/00*    (2006.01)
  *A61C 5/08*    (2006.01)
  *A61C 13/01*   (2006.01)
  *A61C 13/08*   (2006.01)

(56) References Cited

FOREIGN PATENT DOCUMENTS

| | | |
|---|---|---|
| JP | 2009-279268 A | 12/2009 |
| JP | 2010-004755 A | 1/2010 |
| WO | WO 2009/060602 A1 | 5/2009 |

OTHER PUBLICATIONS

Nakatani et al., "Surface Engineering of DLC Thin Films with Controlled Zeta Potential Using Plasma Processing and Evaluation of Cytocompatibility," Journal of Photopolymer Science and Technology, 2009, vol. 22, No. 4, pp. 455-460.

Nitta et al., "Development of Biomimetic DLC with Controlled Zeta Potential Deposited by Plasma Deposited by Plasma Enhanced Chemical Vapor Deposition," vol. fjdkl;afj, (2009).

Nitta et al., "Development of Novel DLC Film using Plasma Techni1que for Medical Material," Journal of Photopolymer Science and Technology, Jun. 22, 2010.

Okamoto et al., "Differentiation Capability Evaluation of Osteoblast by Funcionalized DLC Thin Films with Plasma Processing", Journal of Photopolymer Science and Technology, Jun. 22, 2010.

International Search Report for International Application No. PCT/JP2011/003756 mailed Aug. 23, 2011.

| SAMPLE | SURFACE ELEMENT | | | |
|---|---|---|---|---|
| | N(at. %) | O(at. %) | O-C=O/C | C-O/C |
| A1 | 0.8 | 13.7 | 2.6 | 8.5 |
| A2 | 8.0 | 12.1 | 2.3 | 7.5 |
| A3 | 12.9 | 11.5 | 3.1 | 5.4 |
| A4 | 14.5 | 11.2 | 3.5 | 4.2 |
| A5 | 14.9 | 10.9 | 4.2 | 2.6 |

IMPLANT MATERIAL

CROSS-REFERENCE TO RELATED APPLICATIONS

This application is the U.S. National Phase under 35. U.S.C. §371 of International Application PCT/JP2011/003756, filed Jun. 30, 2011, which claims priority to Japanese Patent Application No. 2010-150093, filed Jun. 30, 2010. The disclosures of the above-described applications are hereby incorporated by reference in their entirety. The International Application was published under PCT Article 21(2) in a language other than English.

TECHNICAL FIELD

The present disclosure relates to implant materials, and more particularly to materials for artificial tooth roots, dentures, and artificial joints which need affinity for bone tissues.

BACKGROUND ART

Implants, such as artificial tooth roots, artificial hip joints, artificial knee joints, and bone connecting materials, which are implanted in living bodies have become more and more important in aging society. As base materials for the implants, titanium and titanium alloys are employed for their high affinity for living bodies, high corrosion resistance, and high mechanical strength. Titanium and titanium alloys, however, are not bonded to living bone tissues, and thus, are not integrated with living bones. If titanium and titanium alloys are implanted in living bodies for a long period, loosening and/or shear can occur. To bond an implant to living bone tissues, there has been an attempt to coat the surface of a base material for an implant with a material having affinity for living bodies.

Hydroxyapatite is most generally used for coating of implants. However, hydroxyapatite has poor adhesion to base materials such as titanium. Accordingly, implants coated with hydroxyapatite have low stability and low durability.

There has also been an attempt to use a diamond-like carbon film (a DLC film) as a coating of an implant (see, for example, Patent Document 1). The DLC film has high adhesion to a base material such as titanium, and thus, can form a stable coating.

CITATION LIST

Patent Document

PATENT DOCUMENT 1: Japanese Patent Publication No. 2002-143185

SUMMARY OF THE INVENTION

Technical Problem

The coating of the DLC film, however, is intended to reduce metal allergy. Therefore, conditions necessary for the DLC film to have a strong bond to living bone tissues are not taken into consideration.

The present disclosure is intended to provide an implant material including a carbonaceous film found by the inventors of the present invention and capable of forming a strong bond to living bone tissues, having high stability and high durability, and capable of forming a strong bond to living bone tissues.

Solution to the Problem

To achieve the object described above, an implant material according to the present disclosure includes a carbonaceous film in which the content of carboxyl carbon in the surface thereof is lower than the content of carbon having a single bond with oxygen and which includes nitrogen atoms.

Specifically, an example implant material includes: a base material; and a carbonaceous film provided on a surface of the base material, wherein the carbonaceous film includes carbon atoms, oxygen atoms, and nitrogen atoms in a surface thereof, the carbon atoms are bonded to the oxygen atoms to form carboxyl carbon and carbon having a single bond with oxygen, a content of nitrogen atoms in the surface of the carbonaceous film is greater than or equal to 8.0 at. %, a content of carbon having a single bond with oxygen in the surface of the carbonaceous film is greater than or equal to 5.4%, and a content of carboxyl carbon in the surface of the carbonaceous film is less than or equal to 3.1%.

The example implant material includes the carbonaceous film in which the content of nitrogen atoms is greater than or equal to 8.0 at. %, the content of carbon having a single bond with oxygen in the surface of the carbonaceous film is greater than or equal to 5.4%, and the content of carboxyl carbon in the surface of the carbonaceous film is less than or equal to 3.1%. Accordingly, the surface of the carbonaceous film has hydrophilicity and the amount of carboxyl carbon having negative charge is small, and thus the surface potential does not greatly decrease. As a result, osteoblasts easily proliferate, and bone formation actively occurs.

In the example implant material, a value obtained by dividing the content of carboxyl carbon by the content of carbon having a single bond with oxygen is preferably less than or equal to 0.6.

Further, a value obtained by dividing, by the content of nitrogen atoms, the value obtained by dividing the content of the carboxyl carbon by the content of carbon having a single bond with oxygen is preferably less than or equal to 0.05.

In the example implant material, the base material may be made of a metal. In this case, the base material is preferably made of titanium or a titanium alloy.

In the example implant material, the base material may be one of an artificial tooth root, a denture, a tooth crown restoration, an artificial bone, or an artificial joint.

Advantages of the Invention

An implant material according to the present disclosure can have high stability and high durability and is capable of forming a strong bond to living bone tissues.

DESCRIPTION OF EMBODIMENT

In an embodiment, an implant refers not only to an artificial tooth root but also to a denture, a tooth crown restoration, or a denture restoration, for example. The implant is not limited to dental use, and includes materials such as artificial bones or artificial joints, which are to be implanted in a living body and need affinity for bone tissues.

A carbonaceous film refers to a film including $sp^2$ carbon-carbon bonding (graphite bonding) and $sp^3$ carbon-carbon bonding (diamond bonding), typified by a diamond-like carbon film (a DLC film). The carbonaceous film may be an amorphous film such as a DLC film or a crystal film such as a diamond film. In general, the carbonaceous film includes $sp^2$ carbon-hydrogen bonding and $sp^3$ carbon-hydrogen bonding, but carbon-hydrogen bonding is not a necessary element. The carbonaceous film may be supplemented with silicon (Si) or fluorine (F), for example.

Figures 1, 2:
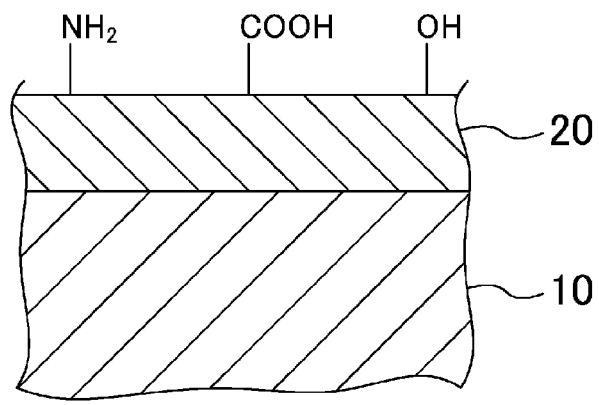
FIG. 1 is a cross-sectional view illustrating an implant material according to an embodiment.
FIG. 2 is a table showing samples of implant materials used for evaluation.

FIG. 1 illustrates a cross-sectional structure of an implant material according to this embodiment. A carbonaceous film 20 with a thickness of about 0.005-3 μm is formed on the surface of a base material 10. A portion of the carbonaceous film 20 at least near the surface thereof contains nitrogen (N) atoms and oxygen (O) atoms. Part of the oxygen atoms form hydroxy groups (OH) and carboxyl groups (COOH). Part of the nitrogen atoms is considered to form amino groups ($NH_2$), for example.

Bonding of an implant to bone tissues (osseointegration) requires bone formation by proliferation and differentiation of osteoblasts on the surface of the implant. To increase treatment effects, proliferation of osteoblasts and bone formation need to proceed quickly. In addition, an implanted implant needs to remain with stability for a long period in a living body. Inventors of the present disclosure found that these necessities can be satisfied by covering a base material such as a metal with a carbonaceous film which includes nitrogen atoms and oxygen atoms in a portion at least near the surface thereof and in which part of oxygen atoms forms hydroxy groups and carboxyl groups.

Specifically, the carbonaceous film of this embodiment has a composition as follows: The content of nitrogen atoms is greater than or equal to about 8.0 at. %. The content of carbon having a single bond with oxygen (C—O) with respect to the total carbon amount is greater than or equal to about 5.4%. The content of carboxyl carbon (O—C=O) with respect to the total carbon amount is less than or equal to about 3.1%. The contents of nitrogen atoms, oxygen atoms, and carbon atoms were analyzed by X-ray photoelectron spectroscopy (XPS). Specifically, the contents (at. %) of the above elements were analyzed as the ratios of a nitrogen-1s (N1s) peak area, an oxygen-1s (O1s) peak area, and a carbon-1s (C1s) peak area where the sum of these areas was 100% in wide scanning of XPS. The contents of carbon having a single bond with oxygen and carboxyl carbon with respect to the total carbon amount were obtained by splitting the C1s peak into a C—C component, a C=O component, a C—O component, and an O—C=O component and dividing the areas of the C—O component and the O—C=O component by the total area of the C1s peak.

Since the surface of the base material is covered with the carbonaceous film in the implant material of this embodiment, high affinity for bone tissues can be obtained, irrespective of the type of the base material. Thus, the base material may be of any type as long as the base material satisfies necessary properties such as strength. For example, a metal such as titanium or a titanium alloy, a resin, or ceramics may be used. The implant material of the present disclosure is applicable to various types of implants that need to have affinity for bone tissues of, for example, artificial tooth roots, dentures, artificial bones, and artificial joints.

The implant material of this embodiment has high affinity for living bone tissues so that the implant material can be bonded to living bone tissues. Accordingly, when an artificial tooth root in which the surface of the base material of, for example, titanium is coated with the carbonaceous film of this embodiment is implanted in a jaw, the artificial tooth root can be firmly bonded to the jaw. Since the surface of the base material is coated with the carbonaceous film, the base material can reduce occurrence of metal allergy reaction. Further, implantation of the artificial tooth root coated with the carbonaceous film in the jaw can be carried out by a general implantation technique. Similar advantages as those obtained in this case can be obtained for other types of implants, e.g., an artificial tooth root whose base material is not titanium and implants except artificial tooth roots.

The carbonaceous film can be formed by chemical vapor deposition (CVD). Alternatively, CVD may be replaced by, for example, spattering, plasma ion implantation, ion plating, arc ion plating, ion beam deposition, or laser abrasion.

Oxygen and moisture in a chamber during and after deposition of the carbonaceous film may cause introduction of oxygen atoms into the surface of the carbonaceous film. Thus, to reduce unintentional introduction of oxygen atoms, a high-purity source gas is used and is supplied with, for example, an adsorption dehydration system for the deposition. For example, in the case of plasma CVD, moisture in the chamber is reduced. In the case of spattering, the purity of an argon gas for use in generation of plasma is set at 99.9999% or more. After completion of the deposition, the carbonaceous film is preferably held in a vacuum for a certain period so that dangling bonds of the carbonaceous film are stabilized. For example, after the temperature of the substrate has reached an ordinary temperature after the deposition, the carbonaceous film is left in a vacuum for at least 10 minutes, preferably 60 minutes or more. Oxygen atoms may be introduced by optimizing conditions for including a predetermined amount of oxygen or moisture or by using dangling bonds.

To adjust the contents of nitrogen atoms and oxygen atoms in a portion at least near the surface of the carbonaceous film, plasma irradiation is performed. To introduce nitrogen atoms into the carbonaceous film, the carbonaceous film is irradiated with plasma of a basic nitrogen-containing compound. Examples of the basic nitrogen-containing compound include organic amines whose general formula is represented as $NR_1R_2R_3$ (where each of $R_1$, $R_2$, and $R_3$ is hydrogen, —$CH_3$, —$C_2H_5$, —$C_3H_7$, or —$C_4H_8$, and $R_1$, $R_2$, and $R_3$ may be the same or different from one another) such as ammonia and also include benzylamine and secondary and tertiary amines thereof. Among these materials, ammonia is preferably used in terms of cost and easiness of handling. The ultimate pressure in the chamber in plasma irradiation is about 0.01-500 Pa. To reduce the influence of oxygen in the air, the ultimate pressure may be about $5\times10^{-3}$ Pa.

To intentionally increase the amount of oxygen atoms contained in the carbonaceous film, oxygen plasma or plasma of an oxygen-containing gas, for example, may be applied. Alternatively, plasma of a mixture of an ammonia gas or the like and an oxygen-containing gas may be used, or the ultimate pressure in application of plasma of, for example, ammonia may be reduced.

In the case of applying plasma of an ammonia gas, the content of nitrogen atoms tends to increase and the content of oxygen atoms tends to decrease as the application time of the plasma increases. As power applied to generate plasma increases, the content of nitrogen atoms tends to increase and the content of oxygen atoms tends to decrease. As the applied power increases, the content of carboxyl carbon tends to increase and the content of carbon having a single bond with oxygen tends to decrease.

The plasma irradiation system may be of any type. The discharge may be performed in any manner, and may be, for example, of a parallel-plate type, an afterglow type, an electromagnetic induction type, or an effective magnetic field type. Conditions for plasma irradiation are not specifically limited. For example, a power supply for plasma generation may use various types of power supply frequencies, e.g., a utility frequency (50 Hz or 60 Hz), a high frequency (a radio frequency), and a microwave frequency. The method for pressure control of, and the supply system for, the source gas are not specifically limited. However, a plasma irradiation condition with an excessively high etching rate might cause damage on the carbonaceous film.

The thickness of the carbonaceous film is not specifically limited, and is preferably in the range of 0.005-3 μm, and more preferably in the range of 0.01-1 μm.

The carbonaceous film can be formed directly on the surface of the base material. To more firmly bond the base material and the carbonaceous film together, an intermediate layer may be provided between the base material and the carbonaceous film. The intermediate layer may be made of various materials depending on the type of the base material, and may be made of a known film such as an amorphous film of a mixture of silicon (Si) and carbon (C), a mixture of titanium (Ti) and carbon (C), or a mixture of chromium (Cr) and carbon (C). The thickness of the intermediate layer is not specifically limited, and is preferably in the range of 0.005-0.3 μm, and more preferably in the range of 0.01-0.1 μm. The intermediate layer is formed by, for example, spattering, CVD, plasma CVD, flame spraying, ion plating, or arc ion plating.

The implant material of this embodiment will be more specifically described hereinafter using examples.

Example

Formation of Carbonaceous Film

A carbonaceous film of a DLC film was formed on the surface of a base material of glass. Evaluation of cells was conducted using a base material with a diameter of 15 mm. The DLC film was formed by chemical vapor deposition (CVD). Specifically, $C_2H_2$ was introduced at a flow rate of 5 sccm ($cm^3$/min., at 1 atmospheric pressure and 0° C.) under a pressure of 3 Pa (35 mTorr) in a chamber in which the base material was placed, and an RF power of about 100 W was applied to an RF electrode.

—Introduction of Oxygen Atoms and Nitrogen Atoms—

To additionally introduce functional groups into the carbonaceous film, plasma irradiation was performed. The plasma irradiation was performed with a plasma irradiation system of a parallel-plate type. The above-described base material was placed in a chamber of the plasma irradiation system, and air was exhausted from the chamber until the pressure in the changer decreases to $5\times10^{-3}$ Pa or less. Then, ammonia was introduced into the chamber at a predetermined flow rate, and an RF power of about 5-50 W was applied between parallel plate electrodes, thereby generating plasma. The gas flow rate was adjusted with a mass flow controller, and the pressure in the chamber during the plasma irradiation was 20 Pa. In addition, RF power was applied by an RF power supply connected through a matching box. Samples having different amounts of introduced nitrogen atoms and oxygen atoms were obtained by changing the application time of RF power and the amount of RF power.

—Analysis of Proportion of Functional Group—

The proportion of functional groups in the carbonaceous film was analyzed by X-ray photoelectron spectroscopy (XPS). An X-ray source was aluminium Kα ray, the acceleration voltage was 14.0 KV, anode power was 25 W, and energy resolution (pass energy) was 23.5 eV. The incident angle of X rays was 45°, and the proportion of functional groups in a portion of the carbonaceous film from the surface to a depth of about 7 nm was analyzed.

The content of nitrogen atoms herein is the ratio (N1s/(C1s+O1s+N1s)) of an N1s peak area to the sum of a C1s peak area, an O1s peak area, and an N1s peak area obtained by wide scanning of an XPS analysis. The state of nitrogen atoms in the surface of the carbonaceous film is unclear. However, it is assumed that these nitrogen atoms form functional groups (nitrogen functional groups) containing nitrogen such as amino groups or amido groups. The content of oxygen atoms herein is the ratio (O1s/(C1s+O1s+N1s)) of an O1s peak area to the sum of a C1s peak area, an O1s peak area, and an N1s peak area obtained by an XPS analysis. In the XPS analyses, the contents obtained from the ratios of the peak areas are expressed in units of at. %.

It is assumed that oxygen atoms form various types of functional groups in the surface of the carbonaceous film. Thus, the C1s peak was divided by curve fitting into a C—O bond (carbon having a single bond with oxygen) component, an O—C=O bond (carboxyl carbon) component, a C=O bond (carbonyl carbon) component, and other components. The ratio of the area of the C—O bond component obtained by curve fitting to the total peak area of the C1s was defined as the content (C—O/C) of carbon having a single bond with oxygen in the total carbon amount. The ratio of the area of the O—C=O bond component to the total peak area of the C1s was defined as the content (O—C=O/C) of carboxyl carbon in the total carbon amount. It is assumed that the C—O bond component includes not only hydroxy groups but also ether bonds, for example. It is also assumed that the O—C=O bond component includes not only carboxyl groups but also ester bonds, for example.

—Evaluation of Cell Proliferation Percentage—

A sterilized sample coated with a carbonaceous film was placed in each well of a 24-hole culture plate, and $5\times10^4$ human osteoblast-like cell line MG63 cells (hereinafter referred to as MG63 cells) were plated, and cultured for 72 hours. As a culture medium, a Dulbecco's modified Eagle's medium (D-MEM) supplemented with 10% fetal bovine serum was used. The cultivation was performed at 37° C. in a 5% carbon dioxide atmosphere. After the cultivation, suspension cells were removed, and an absorbance corresponding to the number of cells was obtained with a commercially available cell counting kit (produced by DOJINDO LABORATORIES: Cell Counting Kit-8) using an absorbance technique. Using a system that has been plated and cultured directly on a plastic culture well as a control, the absorbance ratio of each sample to the control was obtained as a cell proliferation percentage.

—Evaluation of Cell Differentiation—

A sterilized sample coated with a carbonaceous film was placed in each well of a 24-hole culture plate, and $5 \times 10^4$ MG63 cells were plated, and cultured for 72 hours. As a culture medium, a D-MEM supplemented with 1% glutamine and 10% fetal bovine serum was used. The cultivation was performed at 37° C. in a 5% carbon dioxide atmosphere. Then, each well was supplemented with dexamethasone/ascorbic acid as a differentiation stimulator, and was further cultured for 48 hours. Thereafter, the culture medium was removed, and each well was irrigated three times with an HBSS. The cells were then dissolved with a commercially available mammalian protein extraction reagent (M-PER), thereby obtaining a cell lysate.

Using this cell lysate, a total protein mass, alkaline phosphatase (ALP) activity, and an osteocalcin production amount were obtained. To analyze the total protein mass, a commercially available protein assay kit (produced by Thermo Fisher Scientific, Micro BCA™ Protein Assay Kit) employing a bicinchoninic acid technique was used. To analyze ALP activity, a commercially available ALP activity assay kit (produced by Wako Pure Chemical Industries, Ltd., LabAssay™ ALP) was used. To analyze the osteocalcin production amount, a commercially available osteocalcin assay kit employing an enzyme-linked immuno sorbent assay (ELISA) technique was used. A system that has been plated and cultured directly on a well without a sample coated with a carbonaceous film was used as a control.

—Evaluation Result—

Five samples A1-A5 shown in FIG. 2 were prepared by changing RF power of plasma irradiation and the plasma irradiation time. As RF power applied to an electrode and the irradiation time increased, the amount of introduced nitrogen atoms increased and the amount of introduced oxygen atoms decreased. In the functional group containing oxygen atoms, as RF power increased, the amount of carboxyl carbon increased and the amount of carbon having a single bond with oxygen decreased.

Figure 3:
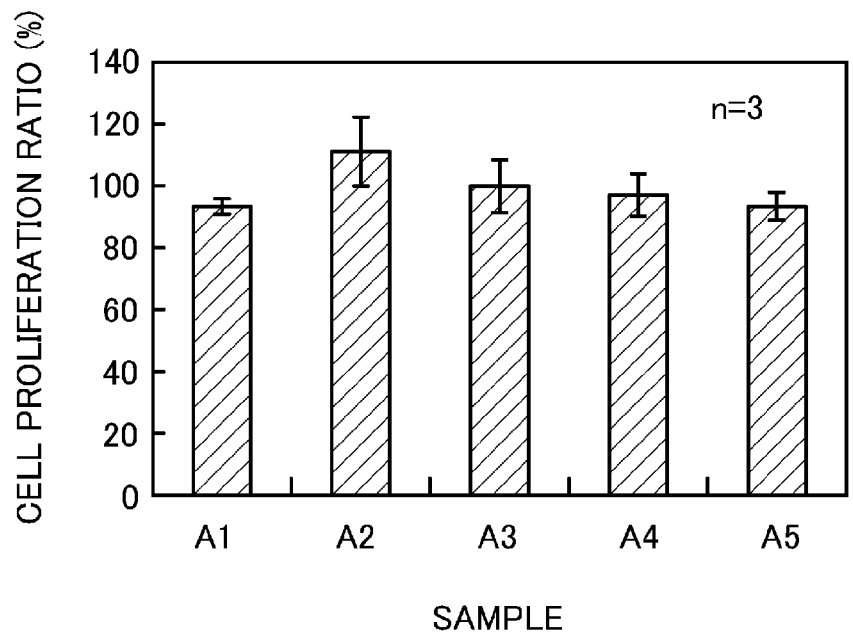
FIG. 3 is a graph showing the cell proliferation percentage in each sample.

FIG. 3 shows the proliferate ratio of MG63 cells in each sample. In each sample, the cell proliferation percentage is 90% or more, and it is clear that each of the samples obtained in this example shows cell proliferation ratios substantially equal to that of the control. In particular, samples A2 and A3 have cell proliferation percentages of 100% or more, and are superior in cell proliferation to the control.

Figure 4:
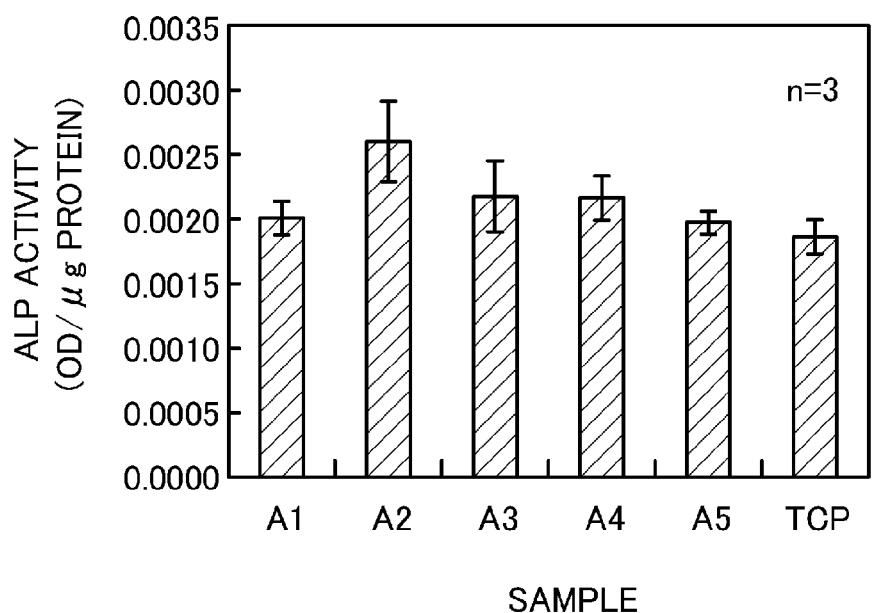
FIG. 4 is a graph showing ALP activity in each sample.

FIG. 4 shows ALP activity in each sample. In FIG. 4, the ordinate represents ALP activity normalized by the total protein mass in the cell lysate. ALP is an enzyme that hydrolyzes phosphoric acid ester, and is known to have high activity when osteoblasts are differentiated to form bone. ALP activity was observed in each of the samples. Each sample shows ALP activity higher than that of the control. Thus, the samples obtained in this example significantly promoted bone formation.

Figure 5:
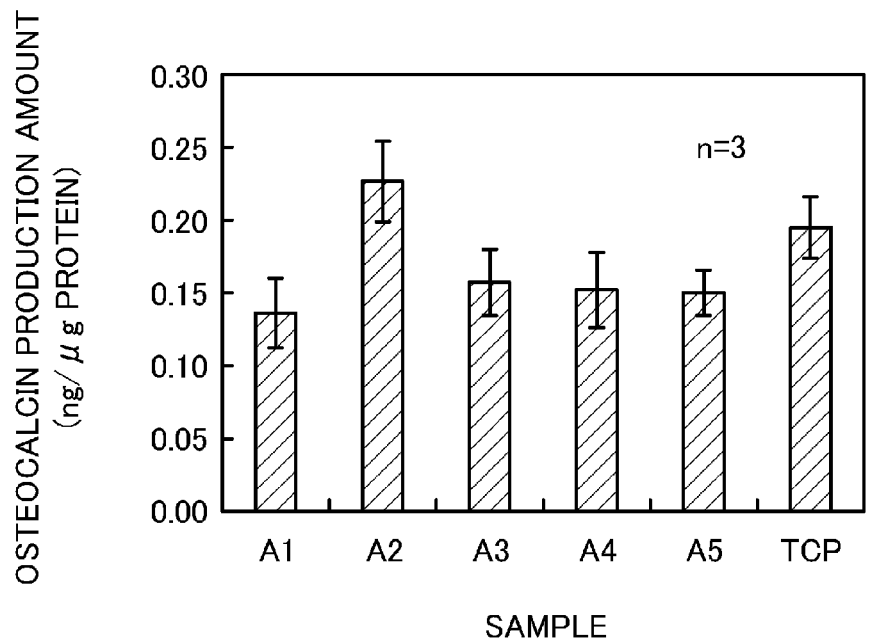
FIG. 5 is a graph showing the osteocalcin production amount in each sample.

FIG. 5 shows the osteocalcin production amount in each sample. In FIG. 5, the ordinate represents the osteocalcin production amount normalized by the total protein mass in the cell lysate. Osteocalcin is considered to contribute to bone turnover, and have a larger osteocalcin production amount when bone formation is promoted in general. In each of the samples obtained in this example, osteocalcin was produced. In particular, sample A2 has a larger osteocalcin production amount than that of the control. Each of the samples obtained in this example, especially sample A2, significantly promoted bone formation.

Figure 6:
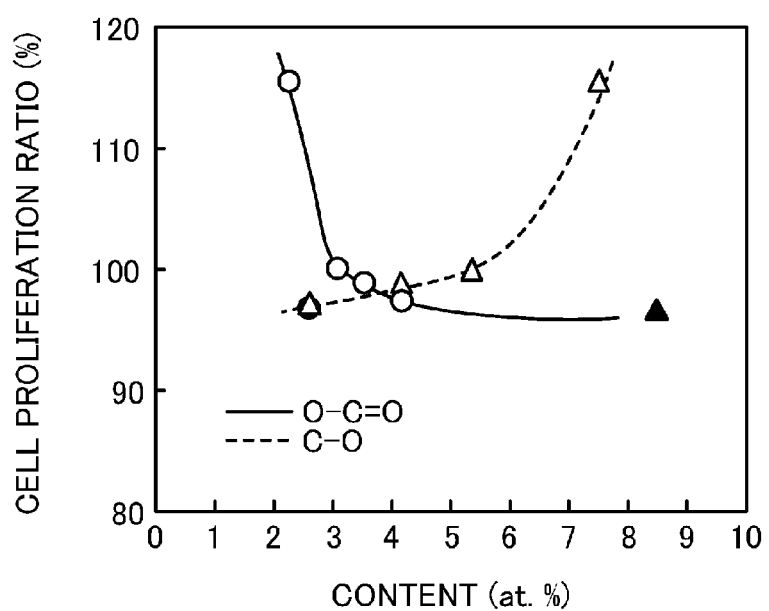
FIG. 6 is a graph showing a relationship between the cell proliferation percentage and each of the content of carboxyl carbon and the content of carbon having a single bond with oxygen.
Figure 7:
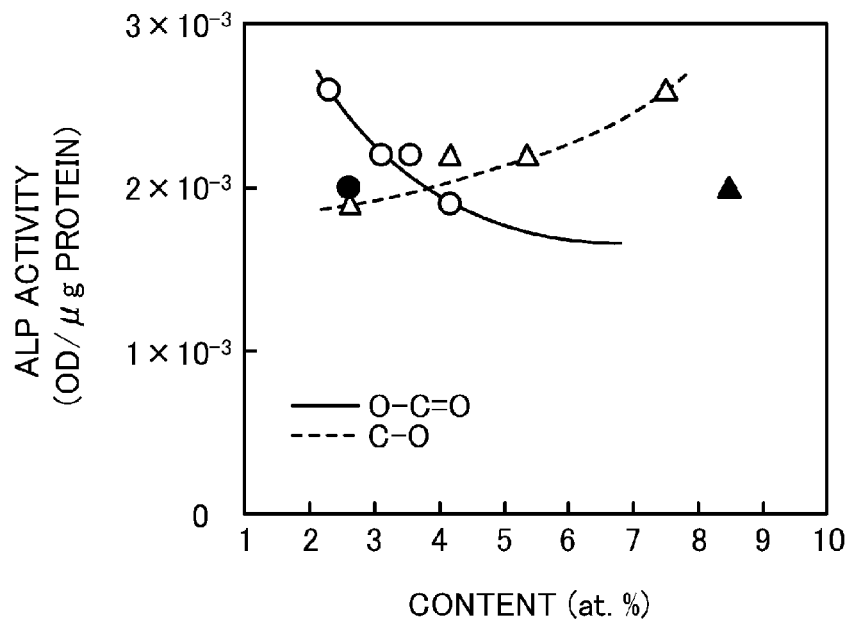
FIG. 7 is a graph showing a relationship between ALP activity and each of the content of carbon having a single bond with oxygen and the content of carboxyl carbon.
Figure 8:
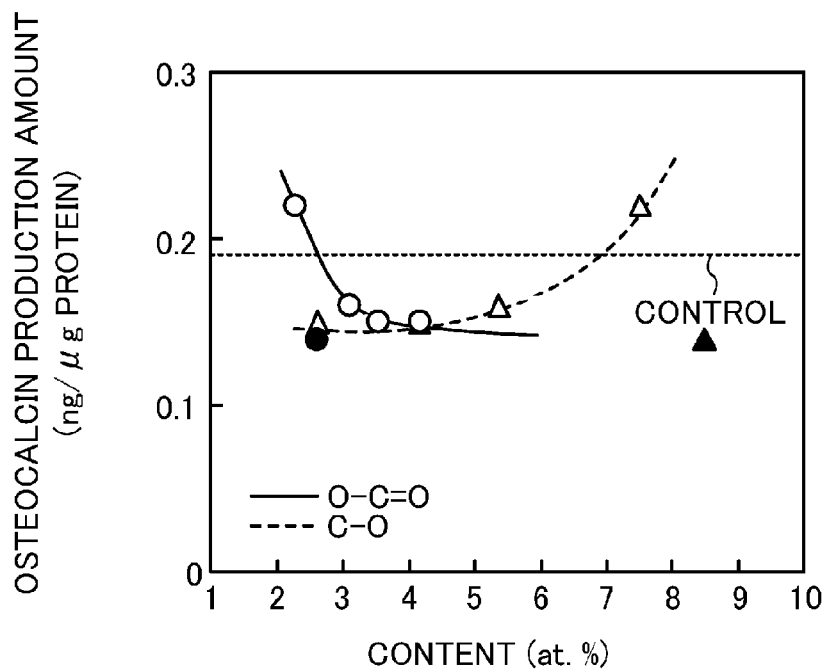
FIG. 8 is a graph showing a relationship between the osteocalcin production amount and each of the content of carbon having a single bond with oxygen and the content of carboxyl carbon.

FIG. 6 shows the cell proliferation percentages plotted with respect to the content of carboxyl carbon and the content of carbon having a single bond with oxygen. As shown in FIG. 6, except for sample A1 indicated by a black circle (●) and a black triangle (▲), the cell proliferation percentage increases as the content of carboxyl carbon decreases or as the content of carbon having a single bond with oxygen increases. FIGS. 7 and 8 respectively show ALP activity and the osteocalcin production amount in the same manner. The ALP activity and the osteocalcin production amount also increase as the content of the carboxyl carbon decreases or as the content of carbon having a single bond with oxygen increases, except for sample A1.

It is assumed that hydrophilicity of the surface of the carbonaceous film increases as the contents of carboxyl carbon and carbon having a single bond with oxygen in this surface increase. However, it is also assumed that negative charge increases as the content of carboxyl carbon increases, resulting in that the surface potential of the carbonaceous film comes to have a large negative value. On the other hand, it is assumed that an increase in the content of carbon having a single bond with oxygen less affects the surface potential of the carbonaceous film than an increase in the content of carboxyl carbon. It is generally known that proliferation and differentiation of cells in the surface of a material are affected by the hydrophilicity and potential in the surface of the material. From this fact, it is assumed that a carbonaceous film containing a high content of hydrophilic functional groups and a low content of carboxyl groups which increase negative charge is preferable for proliferation and differentiation of osteoblasts. As shown in FIG. 2, sample A1 includes a low content of nitrogen atoms. Thus, it is assumed that amino groups are hardly formed in the surface of the carbonaceous film. For this reason, it is assumed that in sample A, the influence of negative charge by carboxyl groups are greater than those in the other samples, and thus, proliferation and differentiation of osteoblasts are inferior to those in the other examples.

Based on the foregoing results, to obtain a carbonaceous film suitable for proliferation and differentiation of osteoblasts, the content of carbon having a single bond with oxygen is greater than or equal to about 5.4%, the content of carboxyl carbon is less than or equal to about 3.1%, and the content of nitrogen atoms is greater than or equal to about 8.0 at. %, near the surface of the carbonaceous film. A lower content of carboxyl carbon is considered to be better. However, a certain amount of carboxyl carbon is introduced during introduction of carbon having a single bond with oxygen, and thus the lower limit of the content of carboxyl carbon is considered to be about 1.0-2.0%. A higher content of carbon having a single bond with oxygen is considered to be better. However, an excessive increase in the amount of introduced oxygen atoms might reduce the amount of introduced nitrogen atoms. Thus, the content of carbon having a single bond with oxygen is preferably about 8.5% or less. A high content of nitrogen atoms is considered not to cause any significant problem. However, experimental data shows the presence of the upper limit of nitrogen atoms capable of being introduced into the surface of a carbonaceous film, and this upper limit is considered to be about 15-20 at. %.

Figure 9:
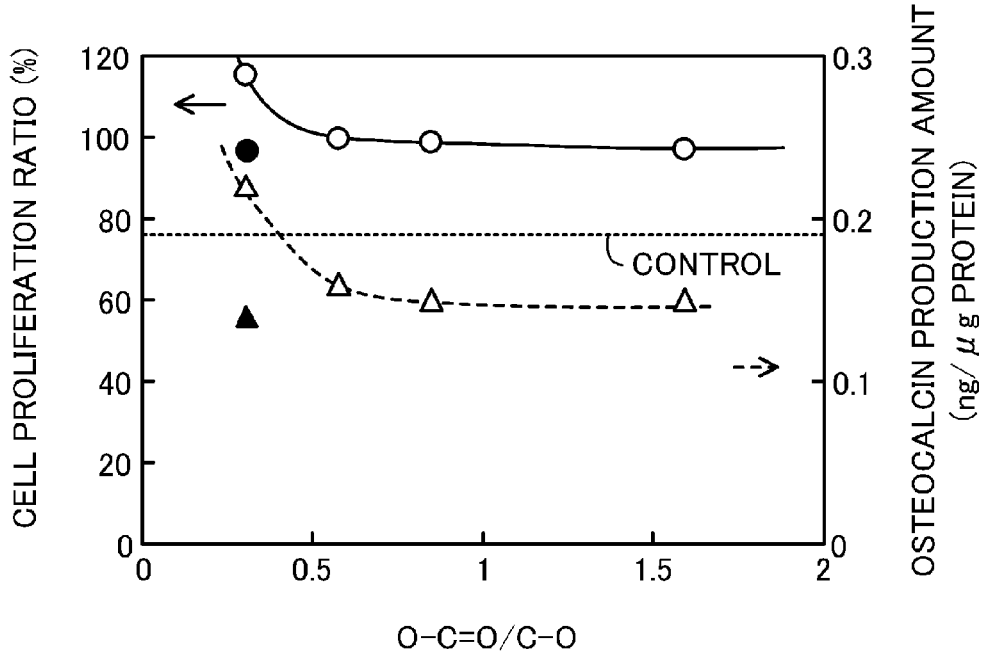
FIG. 9 is a graph showing a relationship between the ratio O—C=O/C—O and each of the cell proliferation percentage and the osteocalcin production amount.

FIG. 9 shows the osteocalcin production amount and the cell proliferation percentage plotted with respect to the ratio (O—C=O/C—O) between the content (O—C=O/C) of carboxyl carbon and the content (C—O/C) of carbon having a single bond with oxygen. In a case where the content of carbon having a single bond with oxygen is greater than or equal to 5.4%, the content of carboxyl carbon is less than or equal to 3.1%, and the content of nitrogen is greater than or equal to 8.0 at. %, the cell proliferation percentage and the osteocalcin production amount increase as the ratio O—C=O/C—O decreases. A similar tendency is observed for the ALP activity. A cell proliferation percentage of 100% or more can be obtained by setting the ratio O—C=O/C—O at about 0.6 or bless. A ratio O—C=O/C—O of about 0.4 or less can make the osteocalcin production amount larger than that of the control. A lower ratio O—C=O/C—O is considered to be better. However, since introduction of carbon having a single bond with oxygen involves introduction of carboxyl carbon, the lower limit of the ratio O—C=O/C—O is expected to be about 0.1.

Figure 10:
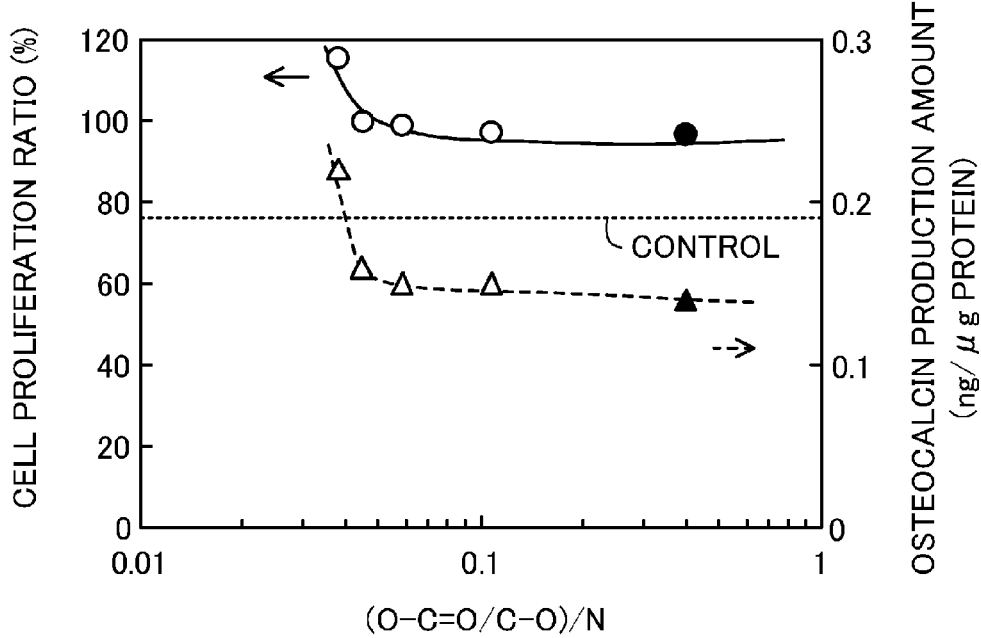
FIG. 10 is a graph showing a relationship between the ratio (O—C=O/C—O)/N and each of the cell proliferation percentage and the osteocalcin production amount.

FIG. 10 shows the cell proliferation percentage and the osteocalcin production amount plotted with respect to the ratio (O—C=O/C—O)/N between the content of carboxyl carbon normalized by the content of nitrogen atoms and the content of carbon having a single bond with oxygen. As the ratio (O—C=O/C—O)/N decreases, the cell proliferation percentage and the osteocalcin production amount increase. A similar tendency is observed for the ALP activity. A cell proliferation percentage of 100% or more can be obtained by setting the ratio (O—C=O/C—O)/N at about 0.05 or less. A ratio (O—C=O/C—O)/N of about 0.04 or less can make the osteocalcin production amount larger than that of the control. A lower ratio (O—C=O/C—O)/N is considered to be better. However, since the lower limit of the ratio O—C=O/C—O is about 0.1 and the upper limit of the content of nitrogen atoms is 15-20 at. %, the lower limit of the ratio (O—C=O/C—O)/N is considered to be about 0.007-0.005.

INDUSTRIAL APPLICABILITY

An implant material according to the present disclosure can be used for an implant having a strong bond to living bone tissues and exhibiting high stability and high durability for a long period, and is useful as a material especially for, for example, artificial tooth roots, dentures, and artificial joints requiring affinity for bone tissues.

DESCRIPTION OF REFERENCE CHARACTERS 10 material
20 carbonaceous film

The invention claimed is:

1. An implant material, comprising:
a base material; and
a carbonaceous film provided on a surface of the base material, wherein
the carbonaceous film includes carbon atoms, oxygen atoms, and nitrogen atoms in a surface thereof,
the carbon atoms are bonded to the oxygen atoms to form carboxyl carbon and carbon having a single bond with oxygen,
a content of nitrogen atoms in the surface of the carbonaceous film is greater than or equal to 8.0 at. %,
a content of carbon having a single bond with oxygen in the surface of the carbonaceous film is greater than or equal to 5.4%, and
a content of carboxyl carbon in the surface of the carbonaceous film is less than or equal to 3.1%.

2. The implant material of claim 1, wherein
a value obtained by dividing the content of carboxyl carbon by the content of carbon having a single bond with oxygen is less than or equal to 0.6.

3. The implant material of claim 2, wherein
a value obtained by dividing, by the content of nitrogen atoms, the value obtained by dividing the content of carboxyl carbon by the content of carbon having a single bond with oxygen is less than or equal to 0.05.

4. The implant material of claim 1, wherein
the base material is made of a metal.

5. The implant material of claim 1, wherein
the base material is made of titanium or a titanium alloy.

6. The implant material of claim 1, wherein
the base material is one of an artificial tooth root, a denture, a tooth crown restoration, an artificial bone, or an artificial joint.

7. A method for producing an implant material, the method comprising the steps of:
preparing a base material;
forming a carbonaceous film on a surface of the base material; and
adjusting a content of nitrogen atoms near a surface of the carbonaceous film, wherein
the step of adjusting the content of nitrogen atoms is the step of irradiating the carbonaceous film with plasma of a basic nitrogen-containing compound,
a pressure in a chamber is less than or equal to $5 \times 10^{-3}$ Pa before the irradiation with the plasma,
a content of nitrogen atoms in the surface of the carbonaceous film is greater than or equal to 8.0 at. %,
a content of carbon having a single bond with oxygen in the surface of the carbonaceous film is greater than or equal to 5.4%, and
a content of carboxyl carbon in the surface of the carbonaceous film is less than or equal to 3.1%.

8. The method of claim 7, further comprising the step of:
stabilizing a dangling bond of the carbonaceous film, after the step of forming the carbonaceous film and before the step of adjusting the content of nitrogen atoms.

* * * * *